United States Patent
Van Berge et al.

(10) Patent No.: US 6,638,889 B1
(45) Date of Patent: Oct. 28, 2003

(54) PROCESS FOR PRODUCING HYDROCARBONS FROM A SYNTHESIS GAS, AND CATALYSTS THEREFOR

(75) Inventors: Peter Jacobus Van Berge, Sasolburg (ZA); Jan Van De Loosdrecht, Sasolburg (ZA); Elsie Adriana Caricato, Sasolburg (ZA); Sean Barradas, Parys (ZA)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 0 days.

(21) Appl. No.: 09/636,787

(22) Filed: Aug. 11, 2000

Related U.S. Application Data

(63) Continuation of application No. PCT/GB99/00527, filed on Feb. 19, 1999.

(30) Foreign Application Priority Data

Feb. 20, 1998 (ZA) ................................................ 98/1440
Dec. 28, 1998 (ZA) ............................................. 98/11882

(51) Int. Cl.[7] ........................... B01J 23/00; B01J 21/00; B01J 23/32; B01J 23/02
(52) U.S. Cl. ...................... 502/300; 502/232; 502/240; 502/263; 502/303; 502/324; 502/325; 502/335; 502/337; 502/340; 502/341; 502/342; 502/343; 502/345; 502/346; 502/349; 502/355
(58) Field of Search ................................ 502/300, 355, 502/240, 263, 232, 303, 349, 345, 346, 342, 343, 324, 340, 341, 325, 335, 337

(56) References Cited

U.S. PATENT DOCUMENTS

| | | | |
|---|---|---|---|
| 5,169,821 A | | 12/1992 | Soled et al. ................ 502/242 |
| 5,424,262 A | * | 6/1995 | de Lasa et al. ............... 502/64 |
| 5,639,798 A | * | 6/1997 | Wilson et al. .............. 518/714 |
| 5,733,839 A | * | 3/1998 | Espinoza et al. ........... 502/336 |

FOREIGN PATENT DOCUMENTS

| | | |
|---|---|---|
| EP | 0141596 | 10/1984 |
| EP | 0586196 | 8/1993 |
| WO | 9720216 | 6/1997 |
| WO | 9815497 | 4/1998 |
| ZA | 982709 | 3/1998 |

OTHER PUBLICATIONS

Baumgarten, E. et al. "Investigation and Modeling of the γ-$Al_2O_3$/Water System" *J. of Colloid and Interface Science* 173 (1995) pp 104–111.

D'Espinose De La Caillerie, J.B. et al. "Alumina/Water Interfacial Phenomena During Impregnation" Preparation of Catalysts VI (Eds. G. Poncelet et al.) (1995) pp 169–183.

Datye, A.K. et al. "Characterization of Surface Structure in Heterogeneous Catalysis by High–Resolution Transmission Electron Microscopy" *Ultramicroscopy* 34 (1990) pp 47–53.

Beguin, B. et al. "Stabilization of Alumina Toward Thermal Sintering by Silicon Addition" *J. of Catalysis* 127 (1991) pp 595–604.

(List continued on next page.)

Primary Examiner—Stanley S. Silverman
Assistant Examiner—Jonas N. Strickland
(74) Attorney, Agent, or Firm—Ladas & Parry

(57) ABSTRACT

A method of treating a catalyst support comprises introducing onto and/or into an untreated catalyst support which is partially soluble in an aqueous acid solution and/or a neutral aqueous solution, Si, Zr, Cu, Zn, Mn, Ba, Co, Ni and/or La as a modifying component. The modifying component is capable, when present in and/or on the catalyst support, of suppressing the solubility of the catalyst support in the aqueous acid solution and/or the neutral aqueous solution. A protected modified catalyst support which is less soluble or more inert in the aqueous acid solution and/or the neutral aqueous solution, than the untreated catalyst support, is thus formed. A method of forming a catalyst from the modified catalyst support is also provided.

18 Claims, 7 Drawing Sheets

OTHER PUBLICATIONS

D'Espinose De La Caillerie, J.B. et al. "Promotion of γ–Alumina Dissolution by Metal Ions During . . . Coprecipitates" Elsevier Science B.V. (1996) (Eds. J.W. Hightower, et al.) pp 1321–1330.

Sarrazin, P. et al. "Interaction of Oxomolybdenum Species With $\gamma_C$–$Al_2O_3$ Modified by Silicon. 1. The $SiO_2/\gamma_C$–$Al_2O_3$ System" J. Phys. Chem. vol. 97 (1993) pp 5947–5953.

Lambert, J–F et al. "Dynamic Phenomena at the Oxide/Water Interface: the Interplay of Surface Charge . . . Reprecipitation." Elsevier Science B.V.(1997) (Eds. G.F. Froment et al.) pp 91–110.

Katada, N. et al. "Mechanism of Growth of Silica Monolayer and Generation of Acidity by Chemical Vapor . . . Alumina" J. Phys. Chem. vol. 98 (1994) pp 7647–7652.

* cited by examiner

Cumulative dissolution profiles of pure and modified titania supports at a solids concentration of 2% (w/w)

PROCESS FOR PRODUCING HYDROCARBONS FROM A SYNTHESIS GAS, AND CATALYSTS THEREFOR

This application is a continuation of application Ser. No. PCT/GB99/00527 filed Feb. 19, 1999.

THIS INVENTION relates to a process for producing hydrocarbons from a synthesis gas, and to catalysts. It relates in particular to a method of treating a catalyst support to form a modified catalyst support, to a modified catalyst support thus formed, to a method of forming a catalyst from the modified catalyst support, to a catalyst thus obtained; to a process for producing hydrocarbons, and to hydrocarbons thus produced.

According to a first aspect of the invention, there is provided a method of treating a catalyst support, which method comprises introducing onto and/or into an untreated catalyst support which is partially soluble in an aqueous acid solution and/or a neutral aqueous solution, Si, Zr, Cu, Zn, Mn, Ba, Co, Ni and/or La as a modifying component which is capable, when present in and/or on the catalyst support, of suppressing the solubility of the catalyst support in the aqueous acid solution and/or the neutral aqueous solution, thereby to form a protected modified catalyst support which is less soluble or more inert in the aqueous acid solution and/or the neutral aqueous solution, than the untreated catalyst support.

The catalyst support may, in particular, be in particulate form. The modifying component is thus present, in the modified catalyst support particles, on the particle surfaces and/or in internal support frameworks of the particles, ie the modifying component is chemically bonded to the particle surfaces and/or to support frameworks of the particles. For example, the modifying component may be chemically bonded to OH (hydroxy groups) on the support surfaces or via the formation of spinel structures with the support.

In principle, any commercially available catalyst support which is partially soluble in an aqueous acid solution and/or in a neutral aqueous solution, can be used. Examples of untreated catalyst supports that can be used are alumina ($Al_2O_3$), titania ($TiO_2$) and magnesia (MgO). When the catalyst support is alumina, any suitable alumina support can, in principle, be used. For example, the alumina support may be that obtainable under the trademark Puralox SCCa 5/150 from CONDEA Chemie GmbH. Puralox SCCa 5/150 (trademark) is a spray-dried alumina support. Similarly, when the catalyst support is titania, any suitable titania support can, in principle, be used. For example, the titania support may be that obtainable under the trademark Degussa P25.

The introduction of the modifying component onto and/or into the catalyst support may include contacting a precursor of the modifying component with the catalyst support, for example, by means of impregnation, precipitation or chemical vapour deposition. Such modifying component precursors include compounds, e.g. salts or alkoxides, containing the modifying component or elements, viz Si, Zr, Cu, Zn, Mn, Ba, Co, Ni, and/or La.

In one embodiment of the invention, the modifying component precursor may, in particular, be a silicon-based modifying component precursor, e.g. an organic silicon compound or agent, so that the modifying component is silicon (Si) The organic silicon compound may be tetra ethoxy silane ('TEOS') or tetra methoxy silane ('TMOS').

When a silicon-based modifying component precursor is used with an alumina catalyst support, it may then be used in a quantity such that the silicon level in the resultant protected modified catalyst support is at least 0.06 Si atoms per square nanometer of the untreated or fresh support, preferably at least 0.13 Si atoms per square nanometer of the fresh support, and more preferably at least 0.26 Si atoms per square nanometer of the fresh support.

The upper limit of the modifying component, e.g. silicon, in the protected modified catalyst support may be set by parameters such as the degree of acidity imparted to the support by the modifying component and/or the porosity of the protected modified catalyst support and/or by the average pore diameter of the protected modified catalyst support. Preferably, the average pore diameter of the protected modified catalyst support as hereinafter described is at least 12 nm, as disclosed in South African Patent No. 96/2759, which is hence incorporated herein by reference thereto. Additionally, if an objective is to obtain, from the protected modified catalyst support, a catalyst having a composition of 30 g Co/100 g $Al_2O_3$, the untreated $Al_2O_3$ catalyst support, and also the protected modified catalyst support, must have a pore volume of at least 0.43 ml/g, as discussed hereinafter with reference to Table 2. The upper limit of the modifying component, e.g. Si, in the protected modified catalyst support is thus to be selected in such a manner that the geometry, e.g. the average pore diameter and porosity, of the protected modified catalyst support is not detrimentally effected to an appreciable extent. If the support acidity is negatively influenced by the modifying component, e.g. as may be the case when silicon is used as the modifying component, then the upper limit of the modifying component in the protected modified support can, instead, be set by the modifying component level at which the support acidity becomes unacceptable.

Thus, when spray-dried Puralox SCCa 5/150 (trademark) alumina is used as the untreated or fresh catalyst support, sufficient silicon-based modifying component precursor is used such that the upper limit of silicon in the resultant protected modified catalyst support is 2.8 Si atoms/$nm^2$ of fresh catalyst support, preferably 2.5 Si atoms/$nm^2$ of fresh catalyst support.

Instead, when spray-dried Puralox SCCa 5/150 (trademark) alumina is used as the untreated catalyst support (ie having a surface area of ca 150 $m^2$/g and a pore volume of ca 0.5 ml/g implying an average pore diameter of ca 13 nm), then the maximum level of silicon may be set in accordance with Table 1.

TABLE 1

Characteristics of silicon modified supports

| Silicon level of modified and calcined $Al_2O_3$ (Si atoms/$nm^2$ of fresh support) | B.E.T. derived geometries of modified and calcined $Al_2O_3$ | | |
|---|---|---|---|
| | Pore volume (ml/g) | Surface area ($m^2$/g) | Average pore diameter (nm) |
| 1 | 0.48 | 155 | 13 |
| 2.5 | 0.48 | 158 | 12 |
| 2.8 | 0.44 | 162 | 11 |
| 7.0 | 0.39 | 157 | 10 |
| 14.8 | 0.25 | 136 | 7 |

The organic silicon compound or agent may be dissolved in an impregnation solvent, which is typically an organic solvent capable of dissolving the silicon compound, such as ethanol, acetone or propanol. The catalyst support may be admixed with the resultant solution to form a treatment mixture. The treatment mixture may be maintained at an elevated temperature for a period of time to impregnate the modifying agent into and/or onto the catalyst support. The elevated temperature may be at or near the boiling point of the impregnation solvent. The impregnation may be effected at atmospheric pressure, and the period of time for which the impregnation is effected may be from 1 minute to 20 hours, preferably from 1 minute to 5 hours. The excess solvent or solution may then be removed, to obtain a modified catalyst support. The removal of the excess solvent or solution may be effected under a vacuum of 0.01 to 1 bar(a), more preferably 0.01 to 0.1 bar(a), and at temperature equal to the boiling point of the solvent, e.g. using known drier equipment, fitted with a mixing device, and of which the jacket temperature is thus higher than the solvent boiling point.

The method may include calcining the silicon-containing modified catalyst support, to obtain the protected modified catalyst support. The calcination of the modified catalyst support may be effected at a temperature from 100° C. to 800° C., preferably from 450° C. to 550° C., and for a period of from 1 minute to 12 hours, preferably from 1 hour to 4 hours.

Calcination after support modification is necessary to decompose organic groups and to obtain the protected modified support. An optimized calcination time can be obtained by infra-red analysis of the modified support after calcination.

In another embodiment of the invention, the modifying component precursor may be an inorganic cobalt compound so that the modifying component is cobalt (Co). The inorganic cobalt compound, when used, may be cobalt nitrate ($Co(NO_3)_2$).

The inorganic cobalt compound may be dissolved in an impregnation solvent, which is typically water or an organic solvent capable of dissolving the cobalt compound, such as ethanol, acetone or propanol. The catalyst support may be admixed with the resultant solution to form a treatment mixture. The treatment mixture may be maintained at an elevated temperature for a period of time to impregnate the modifying agent into and/or onto the catalyst support. The elevated temperature may be at or near the boiling point of the impregnation solvent. The impregnation may be effected at atmospheric pressure, and the period of time for which the impregnation is effected may be from 1 minute to 20 hours, preferably from 1 minute to 5 hours. The excess solvent or solution may then be removed, to obtain a modified catalyst support. The removal of the excess solvent or solution may be effected under a vacuum, preferably a vacuum of 0.01 to 1 bar(a), more preferably 0.01 to 0.1 bar(a), and at a temperature equal to the boiling point of the solvent, e.g. using known drier equipment, fitted with a mixing device, and of which the jacket temperature is thus higher than the solvent boiling point.

The method may then include calcining the cobalt-based modified catalyst support, to obtain the protected modified catalyst support. The calcination of the modified catalyst support may be effected at a temperature from 400° C. to 900° C., preferably from 600° C. to 800° C., and for a period of from 1 minute to 12 hours, preferably from 1 hour to 4 hours to ensure the formation of a relatively water insoluble CoAl spinel layer uniformly covering the total support surface area.

In yet another embodiment of the invention, the modifying component precursor may be an organic zirconium compound so that the modifying component is zirconium (Zr). The contacting of the precursor and the calcination of the modified catalyst support may then be effected in similar fashion to the contacting and calcination hereinbefore described for the cobalt modifying component.

The invention extends to a protected modified catalyst support, when obtained by the method as hereinbefore described.

According to a second aspect of the invention, there is provided a method of forming a catalyst, which method comprises mixing a protected modified catalyst support as hereinbefore described with an aqueous solution of an active catalyst component or its precursor, to form a slurry, and impregnating the protected modified catalyst support with the active catalyst component or its precursor, to form the catalyst.

The active catalyst component precursor may be cobalt nitrate ($Co(NO_3)_2$) so that the active catalyst component in and on the catalyst is cobalt. The support may, as hereinbefore described, be alumina.

The method of forming the catalyst may be in accordance with that described in South Africa Patent No. 96/2759 which is thus incorporated herein by reference. Thus, the mixing of protected modified catalyst support and the active catalyst component or its precursor aqueous solution, and the impregnating, may comprise subjecting a slurry of the catalyst support or carrier, water and the active catalyst component or its precursor to a sub-atmospheric pressure environment, drying the resultant impregnated carrier under a sub-atmospheric pressure environment, and calcining the dried impregnated carrier, to obtain the Fischer-Tropsch catalyst in unreduced form. The unreduced catalyst thus obtained may be washed, e.g. with water, as also described in ZA 96/2759, to remove unwanted contaminants.

However, the water washing described in ZA 96/2759 can be omitted, under certain conditions. For example, if the following two-stage cobalt slurry phase impregnation and calcination of the active catalyst component precursor, in which the carrier or support is alumina, is followed, then water washing of the resultant catalyst is not required.

Thus, in a first stage or step, if it is assumed that the BET pore volume of the alumina support is x ml/g, and that y kg of the support is to be impregnated, the following procedure will ensure proper impregnation:

(1.82xy)kg $Co(NO_3)_2 \cdot 6H_2O$ is dissolved in distilled water, aiming for a final volume of >xy, preferably 2xy, liter. This solution is added to a vacuum drier, and heated to a temperature between 60 and 95° C. To this solution, the total inventory of y kg support material is added at atmospheric pressure whilst continuous mixing of the slurry is maintained, e.g. by means of an internal rotating screw in a conical type vacuum drier. With the gradual application of vacuum, under continuous mixing at a temperature between 60 and 95° C., the loss on ignition (L.O.I.) content of the slurry is reduced (over 3 (or more) hours) from >(136.4x)/(1+1.86x), preferably (236.4x)/(1+1.86x) mass % to the state of incipient wetness. Loss on ignition (L.O.I.) is defined as the mass % loss observed during complete calcination, ie complete decomposition to $Co_3O_4/Al_2O_3$. This gradual drying procedure ensures that the cobalt is quantitatively drawn into the pores of the $Al_2O_3$ support without the occurrence of localized saturation, which results in premature crystallization of cobalt nitrate.

At the state of incipient wetness (L.O.I. of (136.4x)/(1+1.86x)), maximum vacuum (<20 kPa(a)) should be applied whilst ensuring that the bed temperature does not drop below 60° C. under continuous mixing. Once the stage of incipient wetness has been reached, vacuum drying should preferably proceed in an uninterrupted fashion, ideally at the conditions:

>60° C. (but not higher than 95° C.), and a vacuum of <20 kPa(a).

Vacuum drying under these specific conditions should be maintained until a L.O.I. <90% of the L.O.I. value at incipient wetness has been reached.

Direct calcination of this dried material in a fluidized bed, or a rotary kiln, calciner at 200–300° C. (ideally 250° C.) is then preferably effected.

In a second stage or step, if it is assumed that the BET pore volume of the first stage calcined material is x' ml/g, and that y' kg of this material is to be impregnated for a second time, the following procedure will ensure proper impregnation:

A maximum of (1,82x'y') kg $Co(NO_3)_2 \cdot 6H_2O$ can be added during this second impregnation, but this may exceed the aimed for cobalt loading of the catalyst. Table 2 provides the correlation between the pore volume of the starting $Al_2O_3$ (ie x ml/g), and the maximum attainable cobalt loading to be associated with a two-step impregnation procedure:

| Pore volume of starting support material (ml/g) | Maximum attainable cobalt catalyst loading during a catalyst preparation which is limited to 2 impregnation steps |
| --- | --- |
| 0.50 | 35.5 g Co/100 g $Al_2O_3$ |
| 0.49 | 34.7 g Co/100 g $Al_2O_3$ |
| 0.48 | 33.9 g Co/100 g $Al_2O_3$ |
| 0.47 | 33.1 g Co/100 g $Al_2O_3$ |
| 0.46 | 32.4 g Co/100 g $Al_2O_3$ |
| 0.45 | 31.6 g Co/100 g $Al_2O_3$ |
| 0.44 | 30.8 g Co/100 g $Al_2O_3$ |
| 0.43 | 30.1 g Co/100 g $Al_2O_3$ |
| 0.42 | 29.3 g Co/100 g $Al_2O_3$ |
| 0.41 | 28.6 g Co/100 g $Al_2O_3$ |
| 0.40 | 27.8 g Co/100 g $Al_2O_3$ |

If the objective is a final catalyst of composition 30 g Co/100 g $Al_2O_3$, the starting $Al_2O_3$ support must have a pore volume 0.43 ml/g. If, however, the pore volume is larger than 0.43 ml/g, the estimated amount of (1.82x'y')kg $Co(NO_3)_2 \cdot 6H_2O$ should be adjusted in order to ensure the desired catalyst composition. This amount of $Co(NO_3)_2 \cdot 6H_2O$ is dissolved in distilled water aiming for a final volume of >x'y', preferably 2x'y', liter. This solution is added to a vacuum drier, and heated to a temperature between 60 and 95° C. To this solution, the final inventory of y' kg of the first stage material is added at atmospheric pressure, whilst continuous mixing of the slurry is maintained, e.g. by means of an internal rotating screw in a conical type vacuum drier. With the gradual application of vacuum, under continuous mixing at a temperature between 60 and 95° C., the L.O.I. content of the slurry is reduced (over 3 or more hours) to the state of incipient wetness. As stated hereinbefore, this gradual drying procedure ensures that the cobalt is quantitatively drawn into the pores of the support material without the occurrence of localized saturation, which results in premature crystallization of cobalt nitrate.

At the stage of incipient wetness, maximum vacuum (<20 kPa(a)) should be applied whilst simultaneously ensuring that the bed temperature does not drop below 60° C. under continuous mixing. Once the stage of incipient wetness has been reached, vacuum drying should proceed in an uninterrupted fashion, ideally at the conditions:

>60° C. (but not higher than 95° C.), and a vacuum of <20 kPa(a)

Vacuum drying under these specific conditions should be maintained until a L.O.I. <90% of the L.O.I. value at incipient wetness has been reached.

Direct calcination of this dried material in a fluidized bed, or a rotary kiln, calciner at 200–300° C. (ideally 250° C.) is then preferably effected.

During either, or both, of the two abovementioned slurry phase cobalt impregnation steps, a water soluble precursor salt of Pt or Pd may be added, as a dopant capable of enhancing the reducibility of the active component. The mass proportion of this dopant, when used, to cobalt may be between 0.01:100 and 0.3:100.

The invention extends also to a catalyst, when obtained by the method as hereinbefore described.

This catalyst is thus in unreduced form, and requires reduction or activation before it can be used. This may be effected by subjecting it to heat treatment under the influence of a reducing gas such as hydrogen.

According to a third aspect of the invention, there is provided a process for producing hydrocarbons, which includes contacting a synthesis gas comprising hydrogen ($H_2$) and carbon monoxide (CO) at an elevated temperature between 180° C. and 250° C. and an elevated pressure between 10 and 40 bar with a catalyst as hereinbefore described, after activation or reduction thereof, to obtain hydrocarbons, by means of a slurry phase Fischer-Tropsch reaction of the hydrogen with the carbon monoxide.

The invention extends also to hydrocarbons, when produced by the process as hereinbefore described.

It is known that an alumina supported cobalt based slurry phase Fischer-Tropsch catalyst produces a wax product when used in a Fischer-Tropsch reaction of a synthesis gas, comprising hydrogen and carbon monoxide.

Such catalysts have hitherto preferably been produced by slurry impregnation of an alumina support using an aqueous cobalt nitrate precursor solution, of which the pH can vary between 1 and 6. The alumina support partially dissolves in aqueous acid, as well as neutral aqueous solutions. After dissolution the aluminium ions can, in the presence of cobalt ions, re-precipitate as hydrotalcite-like structures, e.g. $Co_6Al_2CO_3(OH)_{16} \cdot 4H_2O$. These amorphous hydrotalcite-like structures are physically adsorbed and loosely bonded to the original alumina surface. The formation of irregular structures on the surfaces of supports present after impregnation of, respectively, alumina with an aqueous nickel nitrate solution, magnesia with an aqueous ruthenium chloride solution and titania with an aqueous platinum chloride solution is also found. This phenomenon is thus not limited to alumina ($Al_2O_3$), but can also be found when using alternative supports such as magnesia (MgO) and titania ($TiO_2$).

A serious problem that can arise when such catalysts, which are thus prepared on untreated supports, are used, as observed during larger scale pilot plant synthesis runs, is the undesired high cobalt content of the wax product. Commercialisation of the slurry phase Fischer-Tropsch synthesis process, using the known untreated alumina supported cobalt catalyst, can result in the wax product containing more than 50 ppm cobalt, after filtration through a Whatmans 42 (trademark) filter paper (hereinafter referred to as "the filtered wax product" or "the filtered wax"). During slurry impregnation of an untreated alumina support, using an aqueous cobalt nitrate solution, cobalt nitrate will deposit on the loosely bonded hydrotalcite-like structures. These cobalt on loosely bonded hydrotalcite-like structures can dislodge during extended runs and contaminate the wax product with cobalt rich ultra fines. These fines, of submicron nature, exit the reactor in the waxy hydrocarbon product. Due to the high cost of cobalt, this is a highly undesirable problem which has thus been solved, or at least alleviated, with this invention. Said alumina support should thus be protected during aqueous slurry impregnation by improving the inertness of the alumina surface, to prevent formation of cobalt ultra fines during Fischer-Tropsch synthesis. This is achieved in the present invention.

The invention will now be described in more detail with reference to the following non-limiting examples and with reference to the drawings.

In the drawings

EXAMPLE 1

1.1 Modification of Alumina Support

A spray-dried Puralox SCCa 5/150 (trademark) alumina support, in the form of spherical particles, obtainable from Condea Chemie GmbH of Überseering 40, 22297, Hamburg, Germany, was used. The surfaces of the support particles were modified with silicon. An impregnation method was used to achieve the modification. Thus, silicon, in the form of TEOS (tetra ethoxy silane) as precursor, was added to ethanol at 60° C., which was thus used as an impregnation solvent. The particulate alumina support was added to this solution, which was then kept at 50° C.–75° C. for 1 hour. Subsequently, the solvent was removed under vacuum at 29.5–88.8 kPa(a), with a jacket temperature of the drier equipment of 95° C. The resultant modified support, in particulate form, was then calcined at 500° C. for 2 hours, to obtain a particulate protected modified catalyst support. Any volatile organic solvent can, in principle, be used provided that TEOS is soluble therein.

A maximum of 2.5 atoms Si/$nm^2$ alumina can be added in one impregnation step using ethanol as impregnation solvent. Acetone can instead be used as solvent. The silica level can be increased by multiple impregnation steps. However, higher levels of silica due to multiple impregnations could lead to multi layers of silica, changing the geometry and/or chemical reactivity of the catalyst support.

Calcination after support modification is necessary to decompose the organic groups and to obtain the protected silicon modified alumina support, through dehydration of the resultant AlOSi[OH]$_3$ species. Infra-red analysis of the modified support after 1, 2 and 12 hours of calcination showed that the methyl and ethyl peaks of the ethoxy groups disappeared after 2 hours of calcination. The optimized calcination time is, therefore, 2 hours.

The addition of silica did not detrimentally alter the geometry of alumina support. The pore volume and surface area of the untreated alumina support were:

Surface area: 150 $m^2$/g
Pore volume: 0.50 ml/g

The support geometry is important with respect to Fischer-Tropsch synthesis performance of the resultant catalyst based thereon, to obtain a desired activity and/or selectivity without the use of synthesis enhancing promoters e.g. the carrier preferably has a specific minimum pore size, e.g. a pore size of at least 12 nm.

1.2 Conductivity Measurements

Alumina dissolves in an aqueous medium at low pH. The dissolution of alumina results in the formation of aluminium ions. As more alumina dissolves, the concentration of aluminium ions increases with time. The increase of aluminium ions with time was followed by monitoring the conductivity at a constant pH of 2. The pH was kept constant by automated addition of a 10% nitric acid solution. The results are set out in FIGS. 1 and 8.

Figure 1:
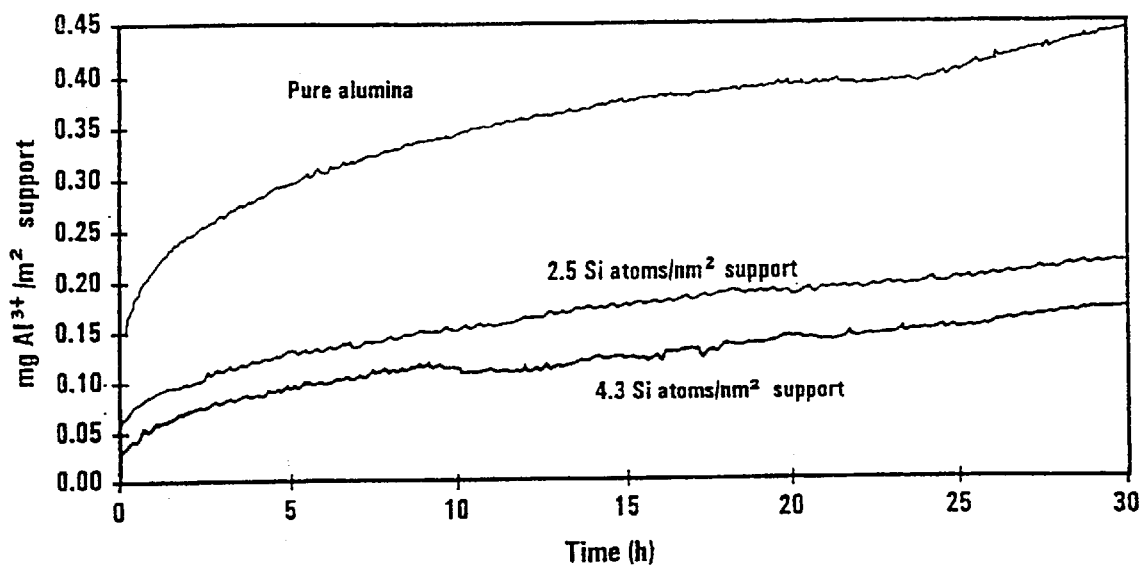
FIG. 1 shows dissolution profiles for a pure or unmodified alumina support, and silica modified alumina supports according to the invention.
Figure 2:
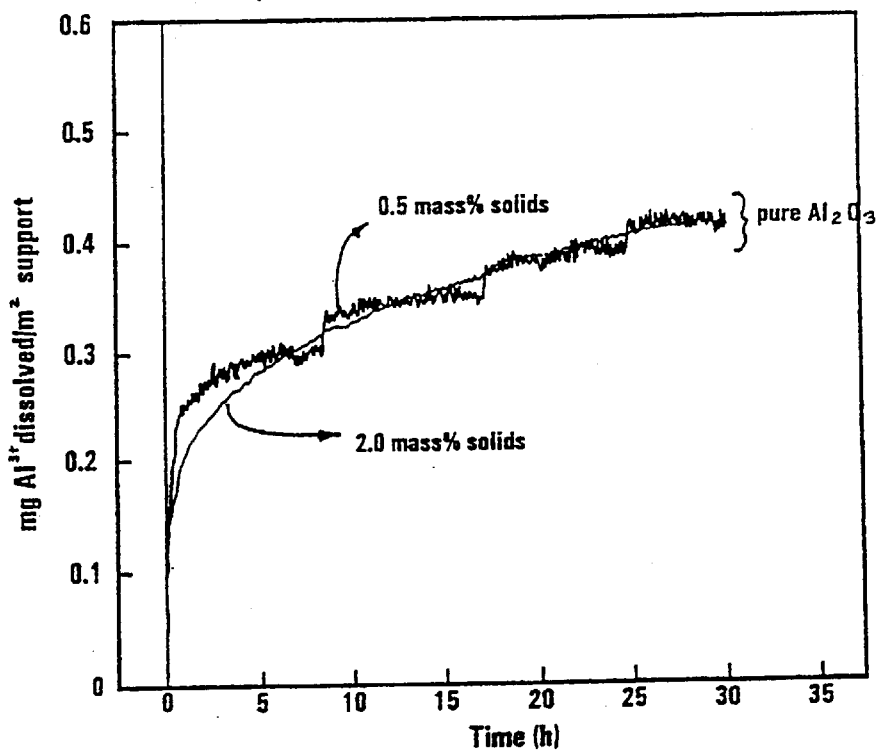
FIG. 2 shows dissolution profiles for an unmodified alumina support, illustrating the influence of solids concentrations.
Figure 8:
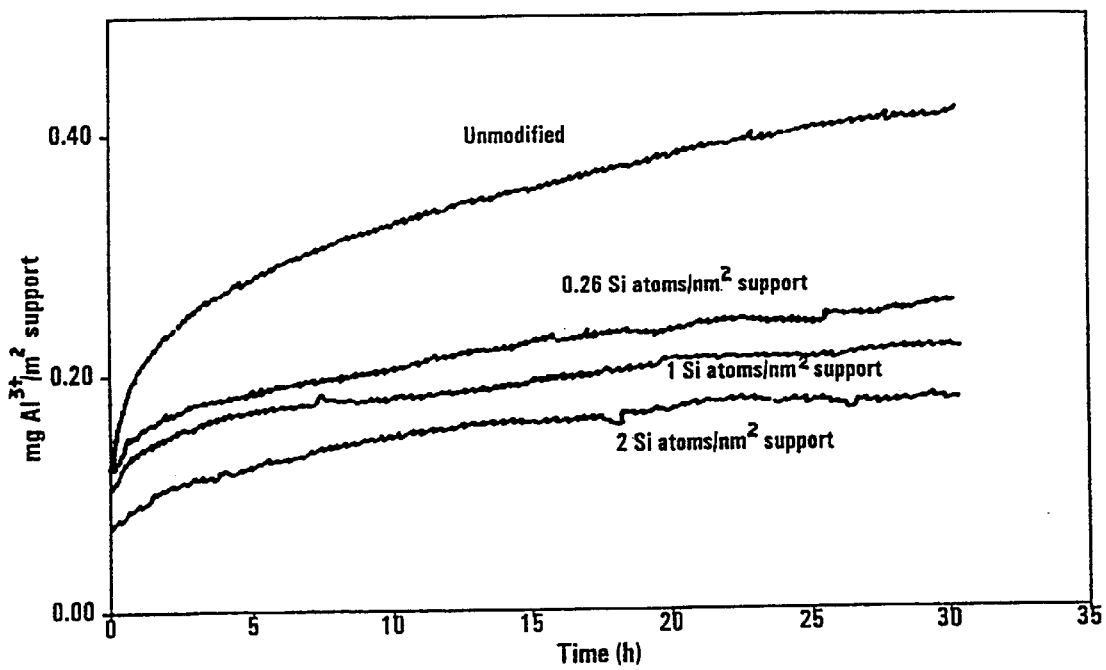
FIG. 8 shows dissolution profiles for a pure or unmodified alumina support, and silica modified alumina supports according to the invention.

In FIGS. 1 and 8, the cumulative mg Al dissolved per $m^2$ fresh support were plotted against time. It can be seen that the unprotected pure alumina dissolves faster than the protected silicon modified alumina. Moreover, a higher level of silica provides better protection against aqueous/acid attack, ie the support modified by 4.3 Si atoms/$nm^2$ fresh alumina exhibits the highest suppression of alumina dissolution. Solid concentrations do not seem to exert a significant influence on the dissolution profile, as shown in FIG. 2

1.3 TEM Experiments

Cobalt based alumina supported catalysts were prepared on the modified alumina supports of 1.1, using the method described in Example 60 of ZA 96/2759. The presence of an amorphous hydrotalcite-like layer was investigated by High Resolution Scanning Electron Microscopy (HRSEM), and Transmission Electron Microscopy (TEM). TEM micrographs identified the presence of an amorphous layer in samples prepared with unmodified alumina supports. Submicron pure boehmite star-like crystals were also observed in these samples, thus confirming dissolution followed by recrystallisation. During slurry impregnation of the catalyst support to obtain the resultant cobalt based catalyst, the active phase (cobalt) will deposit on the physically bonded hydrotalcite-like structures. This active cobalt phase, deposited on the physically bonded hydrotalcite layer, may dislodge during Fischer-Tropsch synthesis and contaminate the wax product with active phase-containing ultra fines. These amorphous layers and the star-like crystals are not present in catalysts prepared on the modified alumina supports. Hence, formation of active phase ultra fines, when using catalysts prepared using the modified supports of the invention, are at least minimized. The amorphous layer is not specific for alumina, but has also previously been found in $TiO_2$ and MgO supported catalysts. In all three cases, the amorphous layers were physically bonded to the support, with the subsequent catalyst preparation steps, ie calcination and/or reduction, unlikely to provide sufficiently high temperature to achieve recrystallization into, e.g. spinels.

1.4 Fischer-Tropsch Synthesis Tests

It would have been expected that the incorporation of silicon into the alumina framework might influence the acidity of the resultant support and could negatively influence the hydrocarbon product selectivity during Fischer-Tropsch synthesis utilizing a catalyst prepared on such supports. However, to prevent the undue introduction of surface acidity of the alumina support, after TEOS impregnation, the modified support was only calcined at <700° C., preferably at 500° C., to remove the organic groups and dehydrate the support without significant incorporation of Si into the $Al_2O_3$ framework, at which temperature it is believed that negligible zeolite type surface acidity will result.

1.5 Laboratory Slurry Chase Fischer-Troosch Synthesis Tests

Between 10 and 30 g properly externally reduced catalyst, prepared on preshaped spray-dried modified or unmodified support, ranging between 38 μm to 150 μm, was suspended in 300 ml molten wax and loaded in a CSTR with an internal volume of 500 ml. The feed gas consisted of hydrogen and carbon monoxide in a $H_2/CO$ molar ratio from 1.5/1 to 2.3/1. This reactor was electrically heated and sufficiently high stirrer speeds were employed so as to eliminate any gas-liquid mass transfer limitations. The feed flow was controlled by means of Brooks mass flow controllers, and space velocities ranging from 2 and 4 $m^3_n$/(h.kg catalyst) were used. GC analyses of the permanent gases as well as the volatile overhead hydrocarbons were used in order to characterize the product spectra.

All catalysts were prepared according to the procedure described for Example 60 of ZA 96/2759 and reduced, prior to synthesis, in a tubular reactor at a pure hydrogen space velocity of 2500 $h^{-1}$ and atmospheric pressure. The temperature was increased from room temperature to 350° C. to 425° C. at a rate of 1° C./min, after which isothermal conditions were maintained for 6 to 16 hours. The results are given in Tables 3 and 4.

TABLE 3 Laboratory CSTR Fischer-Tropsch synthesis performance comparison between catalysts prepared on unmodified, 1.0 Si atom/$nm^2$ and 2.2 Si atoms/$nm^2$ $Al_2O_3$ modified supports

|  | 2.2 Si atoms/$nm^2$ $Al_2O_3$ | 1,0 Si atom/$nm^2$ $Al_2O_3$ | Unmodified alumina |
|---|---|---|---|
| Synthesis conditions |  |  |  |
| Calcined catalyst mass (g) | 21.5 | 24.2 | 23.3 |
| Reactor temperature (° C.) | 220 | 219.6 | 220.4 |
| Reactor pressure (bar) | 20 | 19.9 | 20.6 |
| Time on stream (h) | 20 | 22 | 15 |
| Feed gas composition: |  |  |  |
| $H_2$ (vol %) | 50.1 | 55.5 | 51.2 |
| CO (vol %) | 26.9 | 24.1 | 28.0 |
| $CO_2$ (vol %) | 0.4 | 0.4 | 0.5 |
| Syngas ($H_2$ + CO) space velocity ($m^3_n$/kg cat/h) | 2.2 | 3.0 | 2.2 |
| Rector partial pressures: |  |  |  |
| $H_2$ (bar) | 3.4 | 4.8 | 3.7 |
| CO (bar) | 1.9 | 2.4 | 2.5 |
| $H_2O$ (bar) | 5.5 | 4.7 | 5.6 |
| $CO_2$ (bar) | 0.3 | 0.2 | 0.4 |
| Synthesis performance |  |  |  |
| Conversions: % CO | 76.1 | 66.7 | 70.9 |
| % syngas | 76.4 | 70.1 | 74.5 |
| Productivity (kg HC/kg cat/h) | 0.358 | 0.433 | 0.343 |
| Relative intrinsic specific Fischer-Tropsch activity | 1.04 | 1.08 | 1.00 |
| % C · atom $CH_4$ selectivity | 6.6 | 6.7 | 4.4 |
| % CO of total amount of CO converted to $CO_2$ | 3.9 | 1.8 | 4.3 |

During the laboratory CSTR Fischer-Tropsch slurry phase synthesis runs reported in Table 3, prepared on either unmodified or on silica modified alumina, the filtered wax produced remained white and the cobalt content was below the detection limit (<1 ppm).

Having applied a reported cobalt based Fischer-Tropsch kinetic equation, such as:

$$r_{FT} = (k_{FT} P_{H2} P_{co})/(1+\beta P_{co})^2$$

the Arrhenius derived pre-exponential factor of $k_{FT}$ was estimated for each of the 3 reported runs. By defining the relative intrinsic specific Fischer-Tropsch activity as (pre-exponential factor of Si modified catalyst)/(pre-exponential factor of the unmodified catalyst), it can be concluded that support modification did not affect the intrinsic activities.

TABLE 4

Laboratory CSTR Fischer-Tropsch reactor wax (i.e. $C_{19+}$) selectivity
comparison between catalysts prepared on an unmodified and a modified alumina of
composition 2.2 Si atoms/nm$^2$ of fresh support

| Synthesis conditions | | | | | | | | Estimated $C_{19+}$ mass % selectivities | |
|---|---|---|---|---|---|---|---|---|---|
| Temp | Pressure | Feed Composition (vol %) | | Syngas space velocity | Reactor partial pressures (bar) | | | Measured for a 2,2 Si atoms/nm$^2$ support | Model prediction for a unmodified support prepared |
| (° C.) | (bar) | H$_2$ | CO | (m$^3_n$/kg cat.h) | H$_2$ | CO | H$_2$O | prepared catalyst | catalyst |
| 219 | 20.0 | 41.9 | 26.6 | 2.46 | 4.6 | 4.0 | 2.4 | 53.9 | 52.8 |
| 231 | 20.2 | 43.4 | 27.6 | 3.70 | 4.2 | 3.9 | 3.1 | 44.8 | 53.6 |
| 231 | 20.3 | 43.1 | 26.6 | 3.75 | 4.1 | 3.6 | 3.1 | 48.2 | 50.4 |
| 231 | 20.5 | 38.7 | 17.8 | 2.03 | 2.2 | 1.1 | 3.3 | 22.6 | 11.2 |
| 231 | 20.5 | 39.3 | 17.4 | 2.09 | 2.4 | 1.1 | 3.6 | 23.4 | 10.0 |
| 231 | 20.9 | 55.4 | 25.9 | 3.35 | 5.0 | 2.4 | 5.4 | 38.5 | 26.1 |
| 231 | 21.0 | 43.8 | 21.7 | 3.40 | 4.2 | 2.2 | 3.6 | 42.2 | 25.9 |
| 230 | 19.9 | 49.8 | 32.6 | 3.88 | 6.0 | 5.1 | 3.1 | 51.9 | 58.2 |
| 230 | 19.5 | 52.0 | 27.3 | 2.19 | 3.5 | 2.5 | 5.2 | 39.9 | 36.2 |
| 230 | 19.8 | 49.9 | 25.0 | 2.23 | 4.6 | 2.5 | 4.1 | 36.3 | 29.7 |

Figure 3:
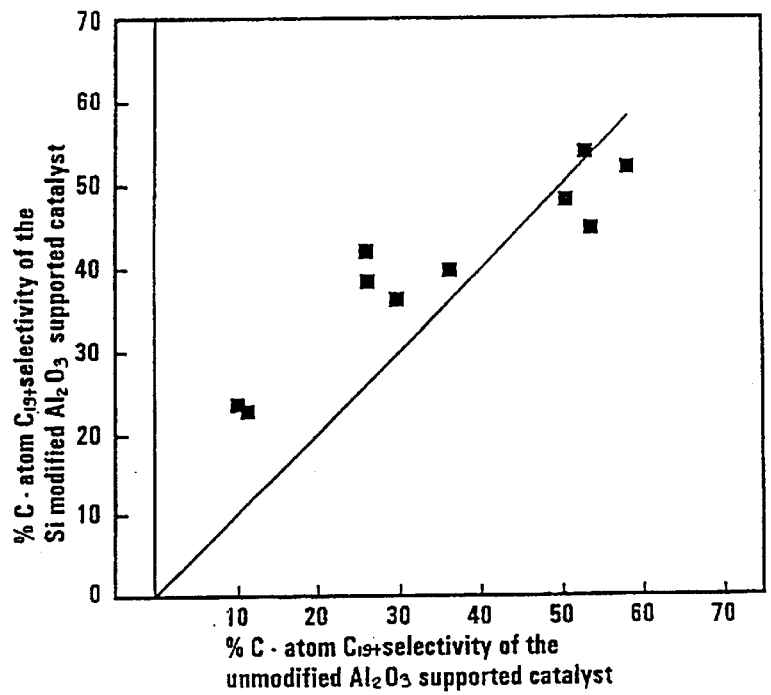
FIG. 3 shows a parity plot of percentage carbon atom $C_{19+}$ selectivities of a 20 mass % cobalt supported catalyst prepared on a Si modified alumina support (surface concentration of 2.5 Si atoms per $nm^2$ support and its unmodified alumina supported equivalent.

A graphical illustration of Table 4 is presented in FIG. 3 indicating that at conditions favouring high molecular weight selectivities, it could be concluded that the catalyst prepared on a Si modified support does under achieve somewhat.

Figure 4:
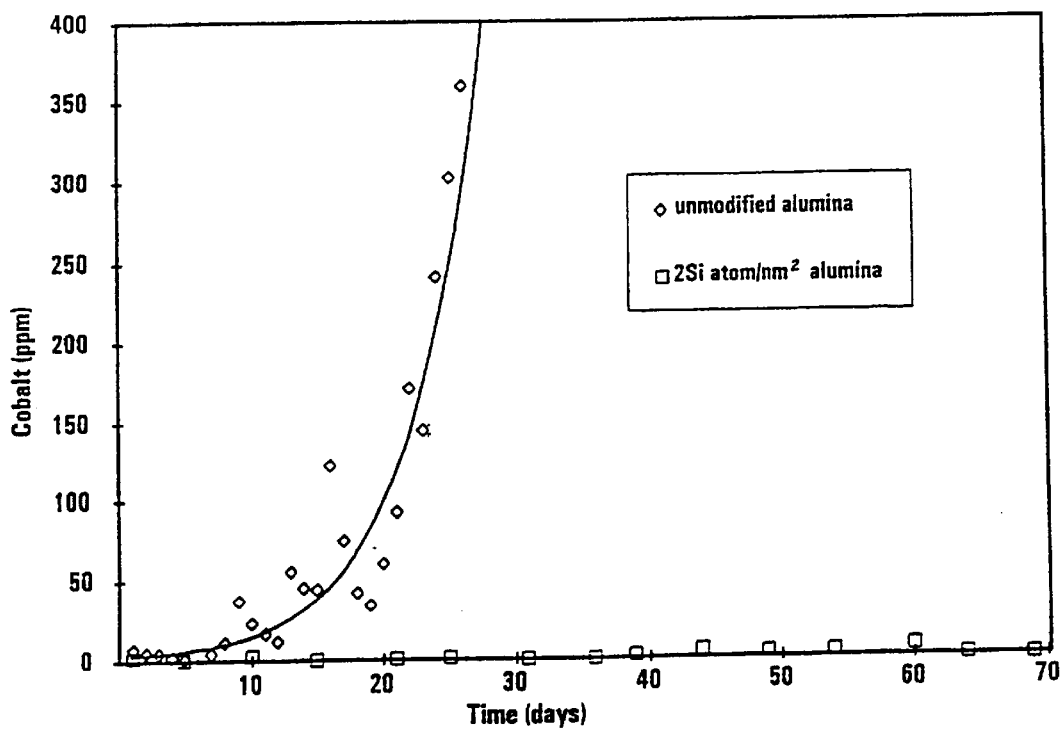
FIG. 4 shows the cobalt content of filtered waxes, produced on Pilot Plant scale, using supported cobalt catalysts obtained from unmodified alumina supports, and silica modified alumina supports according to the invention.

During a confidential Pilot Plant Fischer-Tropsch synthesis test run, using 5 kg of catalyst prepared on unmodified alumina, in a 11 m high bubble column slurry reactor (ie Pilot Plant scale) with an external recycle, the filtered wax product turned grey after about 10 days on line and the cobalt content increased to 350 ppm after 25 days on line, as shown in FIG. 4.

Figure 5:
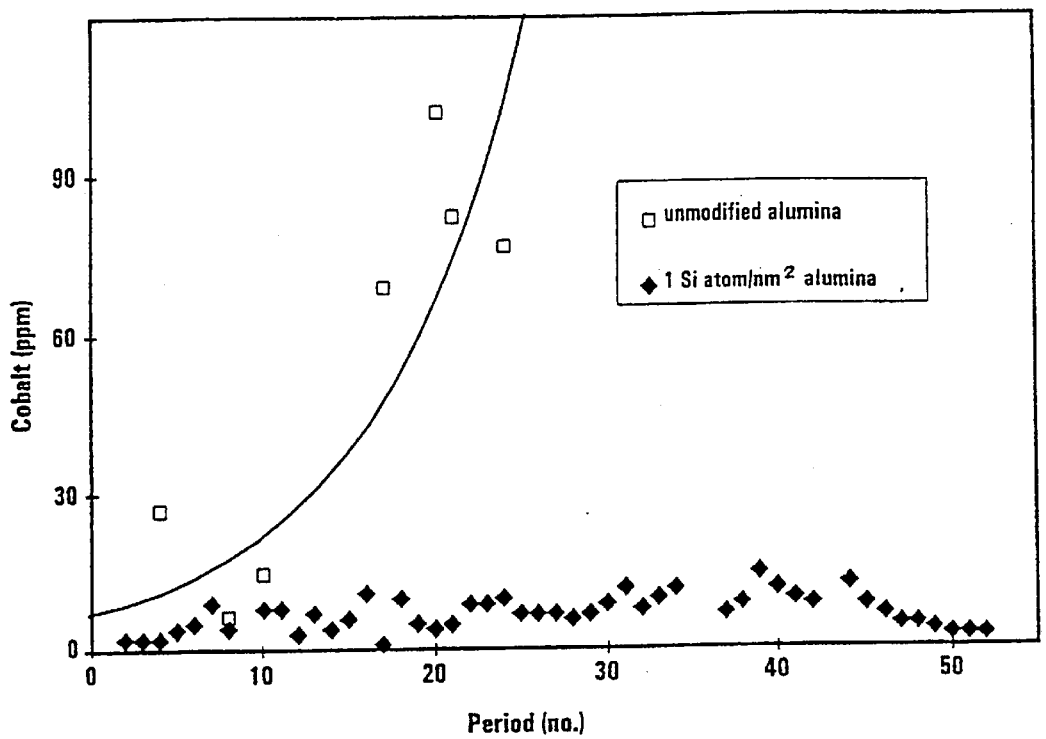
FIG. 5 shows the cobalt content of filtered waxes produced on Works Pilot Plant scale using supported cobalt catalysts obtained from unmodified alumina as well as silica modified alumina in accordance with the invention.

A similar observation was made during a confidential test run, in a 25 m high bubble column slurry reactor (ie Works Pilot Plant scale) with sufficient backmixing to ensure a uniform catalyst suspension, using 1500 kg of catalyst prepared on unmodified alumina, as shown in FIG. 5.

In both these Pilot Plant reactors, the mechanical stress on the catalyst is significantly more severe than in the laboratory CSTR reactor.

The presence of a high cobalt content in the wax product is believed to be due to the dislodgement of cobalt crystallites deposited on top of the physically bonded cobalt containing hydrotalcite-like structures, present in the catalyst after aqueous slurry impregnation, when the catalyst is prepared from an unmodified support.

Pilot Plant synthesis test runs with catalysts prepared on 1.0 Si atoms/nm$^2$ Al$_2$O$_3$ and 2.2 Si atoms/nm$^2$ Al$_2$O$_3$ modified alumina support showed a substantial improvement with respect to the submicron cobalt particulate contamination in the filtered wax product. After 70 days on line the catalyst with 2 Si atom/nm$^2$ Al$_2$O$_3$ did not show any cobalt in the filtered wax product (FIG. 4). A test run in the Works Pilot Plant bubble column slurry reactor with 1000 kg of catalyst prepared on 1.0 Si atoms/nm$^2$ Al$_2$O$_3$ modified alumina support also showed a dramatic improvement in the cobalt content in the wax product compared to the run with the catalyst on the unmodified support (FIG. 5). The cobalt content in the wax product was on average between 5 and 10 ppm.

From the Works Pilot Plant synthesis tests, it can be seen that the improvement of the inertness of the alumina support by modifying it with silica, as was shown by TEM and conductivity measurements, also prevented the dislodging of ultra fine cobalt rich particulates during slurry phase Fischer-Tropsch synthesis.

EXAMPLE 2

2.1 Modification of Alumina Support

Cobalt, in the form of cobalt nitrate as precursor, was added to acetone at 45° C. Acetone was thus used as an impregnation solvent. A particulate alumina support was added to this solution, and the resultant mixture kept at 60° C. for 10 minutes. The solvent was then removed under a vacuum of 3 kpa(a) with a jacket temperature of the drier equipment at 95° C. The resultant modified support was subsequently calcined at 800° C. for 2 hours to obtain a protected modified catalyst support.

The high calcination temperature was aimed at obtaining a spinel-type protected modified support.

Figure 6:
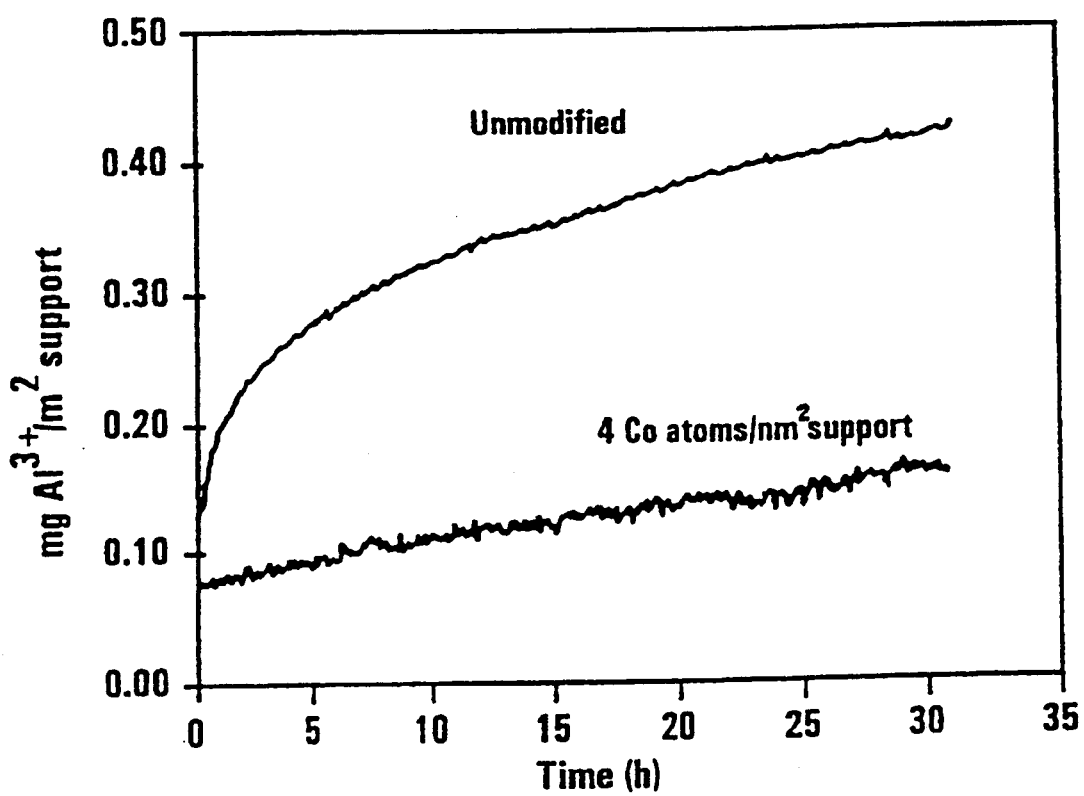
FIG. 6 shows dissolution profiles for an unmodified alumina support, and a cobalt modified support according to the invention.

In FIG. 6, the dissolution profiles for untreated and cobalt modified alumina supports, in accordance with this Example, are plotted. FIG. 6 shows that modification of the untreated alumina support with cobalt, increased the resistance to dissolution.

The addition of cobalt had a small effect on the geometry of the support:

| Before modification: | Surface area: | 155 m$^2$/g |
|---|---|---|
| | Pore volume: | 0.48 cc/g |
| After modification: | Surface area: | 154 m$^2$/g |
| | Pore volume: | 0.43 cc/g |

EXAMPLE 3

3.1 Modification of Titania Support

Particulate titanium dioxide (Degussa P25 (trademark)) support was calcined at 650° C. for 16 hours, spray dried and classified to 75–150 micron. The support had a rutile content of 80% and a surface area of 27 m$^2$/g.

This support was also modified in the same fashion as described in Example 1 by addition of TEOS and calcination at 500° C. The silicon content was analyzed as 4.5 Si atoms/nm$^2$ fresh support.

Titania dissolves in an aqueous acid medium. The dissolution of titania results in the formation of titanium ions. The increase of titanium ions with time was followed by monitoring the conductivity at a constant pH of 2. The pH was kept constant by automated addition of a 10% nitric acid solution.

Figure 7:
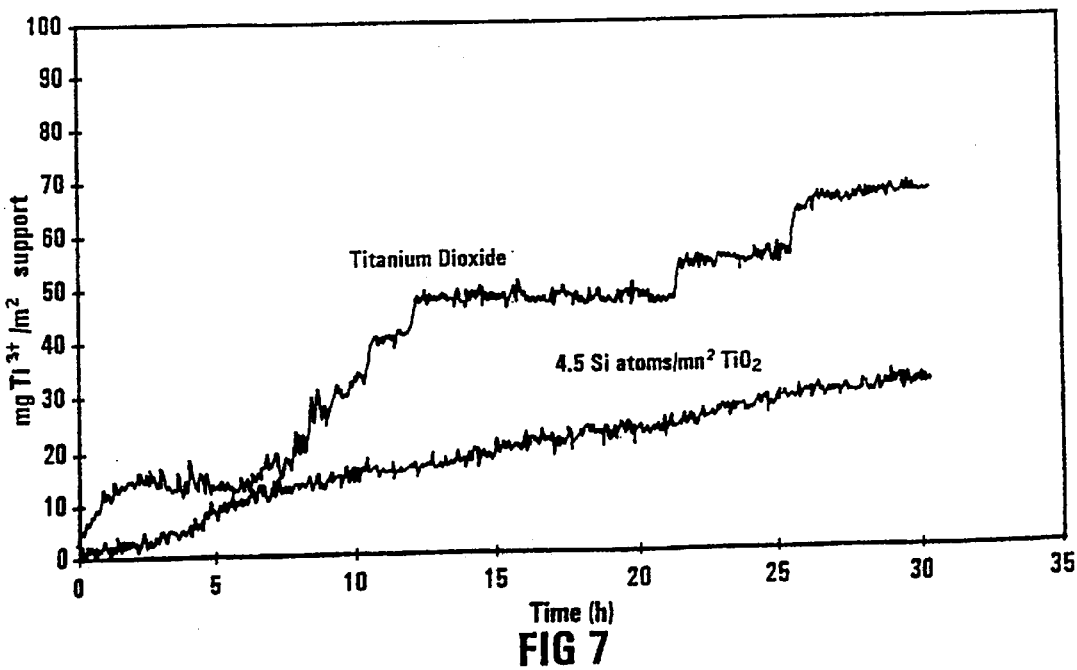
FIG. 7 shows dissolution profiles for a pure or unmodified titania support, and silica modified titania supports according to the invention.

In FIG. 7, the dissolution profiles of titania are plotted. This indicated that modification of the pure titania did bring along an increase in resistance to dissolution.

EXAMPLE 4

A Puralox 5/150 alumina support surface was modified with silicon. The method of Beguin B Garbowski E and Primet M, J. Catal. 1991, 127, 595 was used as background for the silicon modification or impregnation method. Silicon, using TEOS (tetra ethoxy silane) as modifying component precursor, was added to ethanol at 50–75° C. which was thus used as an impregnation solvent. Alumina was added to this solution, which was then kept at 50–75° C. for 1 hour. Subsequently, the solvent was removed under vacuum at 29.5–88.8 kPa(a) with a jacket temperature of the drier equipment of 95° C. The modified support obtained was then calcined at 500° C. for 2 hours. Any organic solvent can be used as long as TEOS is soluble in it.

The amount of precursor was such that the final silicon level was 0.26 Si atoms/nm$^2$ of fresh alumina support.

EXAMPLE 5

A modified support was prepared in the same way as Example 4 except that the amount of precursor added was such that the final silicon level was 1.0 Si atoms/nm$^2$ of fresh alumina support.

EXAMPLE 6

A modified support was prepared in the same way as Example 4 except that the amount of precursor added was such that the final silicon level was 2.0 Si atoms/nm$^2$ of fresh alumina support.

EXAMPLE 7
Conductivity Measurements

FIG. 8 shows that the dissolution of alumina is also suppressed by the introduction of relatively small quantities of silicon. Levels as low as 0.26 Si atoms/nm$^2$ of fresh alumina support offer protection against dissolution, with increasing protection as the silicon level increases.

EXAMPLE 8

Silicon levels of 2.5 atoms/nm$^2$ of fresh alumina support were found to be the maximum attainable level to be achieved via a single impregnation step as per Example 1. Silicon levels of 2.8 Si atoms/nm$^2$ fresh support, 4.3 Si atoms/nm$^2$ fresh support, 7.0 Si atoms/nm$^2$ fresh support and 14.8 Si atoms/nm$^2$ fresh support were prepared as described in Example 4 with the exception that multiple impregnation steps were employed with a 500° C. for 2 hours calcination treatment after each consecutive impregnation step.

EXAMPLE 9
Fischer-Tropsch Synthesis Test

Figure 9:
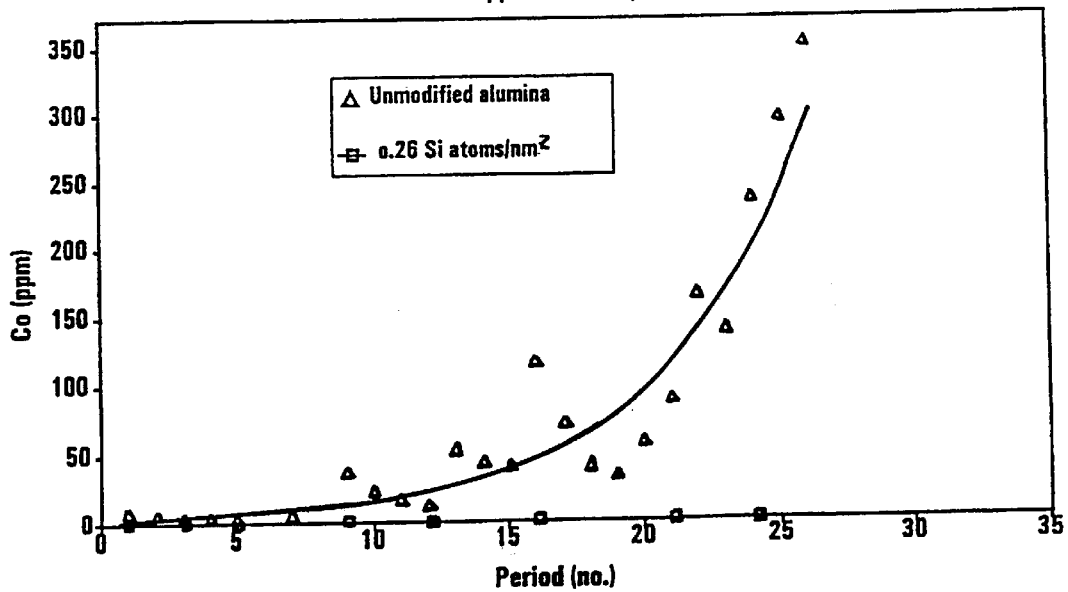
FIG. 9 shows the cobalt content of filtered waxes produced on Pilot Plant scale using supported cobalt catalysts obtained from unmodified alumina as well as from silica modified alumina in accordance with the invention.

A pilot plant batch (ca 30 kg) of catalyst was prepared on a particulate alumina support which had been modified with the lowest silicon level, ie 0.26 Si atoms/nm$^2$ of fresh alumina support. This catalyst was tested during a confidential pilot plant Fischer-Tropsch synthesis run in a 11 m high bubble column reactor with an external recycle. FIG. 9 shows a comparison of the cobalt content in the secondary filtered wax between this run and a run performed using a catalyst on an unmodified support. No cobalt was shown in the filtered wax product of the modified catalyst.

Thus a level of 0.26 Si atoms/nm$^2$ of alumina support successfully suppressed the dissolution characteristics to such an extent that the formation of cobalt rich ultrafine particulate material during slurry phase Fischer-Tropsch synthesis was successfully suppressed.

EXAMPLE 10

Zirconium, in the form of zirconium isopropoxide, was added under an inert atmosphere to isopropanol. Isopropanol was thus used as the impregnation solvent. A particulate alumina support was added to this solution, and the mixture stirred at 60° C. for 1 hour. The solvent was then removed under a vacuum of 3 kPa(a) with a jacket temperature of the drier equipment at 95° C. The resultant modified support was subsequently calcined at 600° C. for 2 hours to obtain a protected modified catalyst support. The amount of modifying component was found to be 0.1 Zr atoms per square nanometer fresh support.

Figure 10:
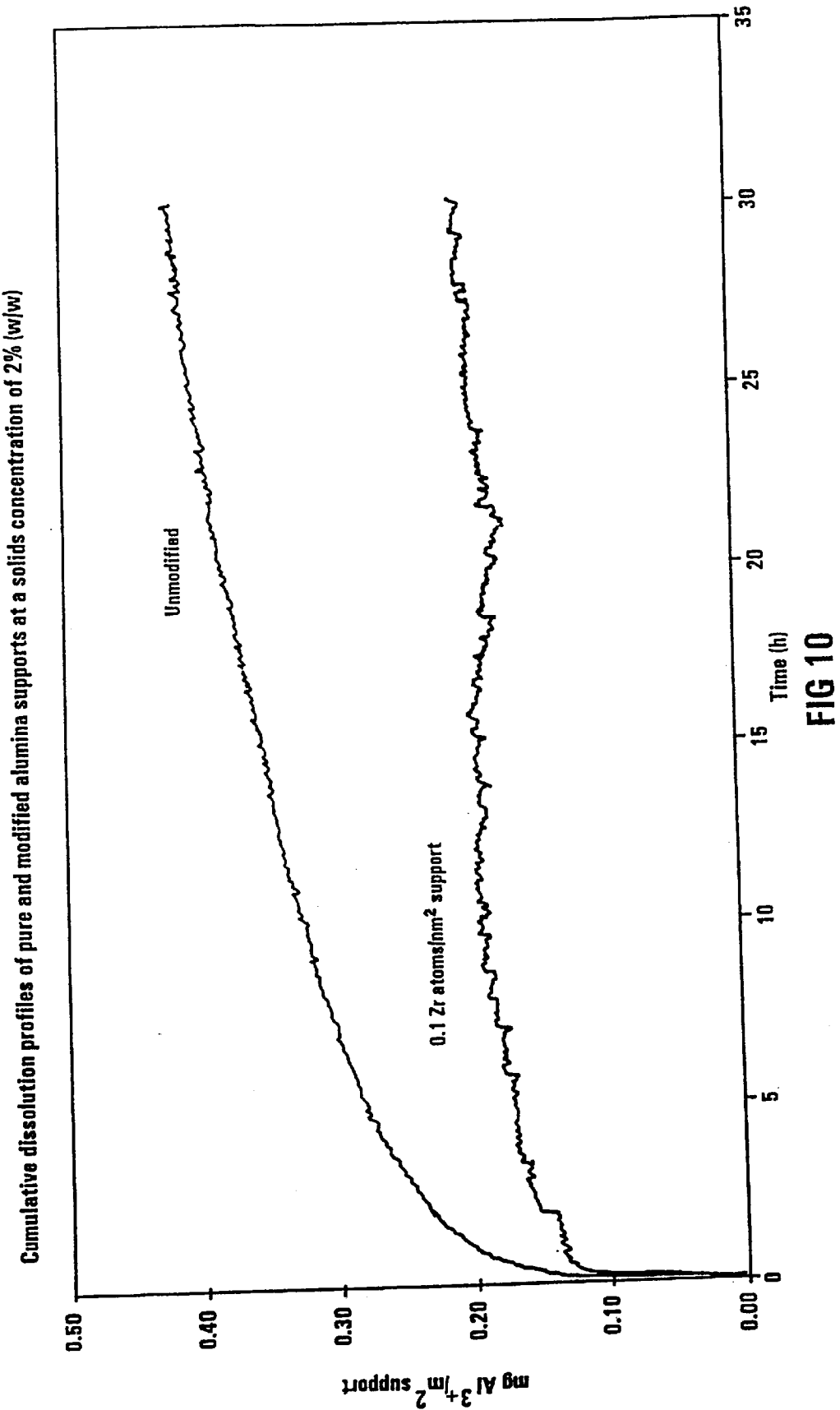
FIG. 10 shows dissolution profiles for a pure alumina support, and a zirconium modified alumina support according to the invention.

In FIG. 10, the dissolution profile of the fresh Condea Puralox SCCa 5/150 (trademark) alumina support is plotted against the dissolution profile of the zirconium modified alumina support described above. The addition of zirconium to the fresh support thus improved the resistance of the support to dissolution and aqueous/acid attack.

EXAMPLE 11

Dissolution profiles of different alumina crystal phases were determined and compared to the commercially available Condea Puralox SCCa 5/150 (trademark) alumina support, which was used in, for example, Example 1. The results are given in FIG. 10.

The crystal phases that were tested, were delta, gamma and alpha alumina. The pure aluminas were prepared by calcination of the raw alumina material boehmite or Al(OH)$_3$ at different temperatures; gamma alumina being obtained at the lowest calcination temperature between 500° C. to 700° C., followed by delta alumina at a calcination temperature of 850° C., and alpha alumina at a calcination temperature of 1150° C.

The surface area of these supports is greatly affected by the calcination temperature. Thus, a support, which contains mostly gamma alumina, will have the highest surface area, which is desirable in heterogeneous catalysis. The gamma alumina support, however, exhibited a higher dissolution behaviour after 30 hours compared to delta and alpha alumina. It is known that OH groups present on the surface of an alumina support can act as initiators for aluminium extraction and therefore dissolution. Calcination of alumina at high temperatures causes dehydration of the support and therefor loss of surface hydroxyl groups.

Figure 11:
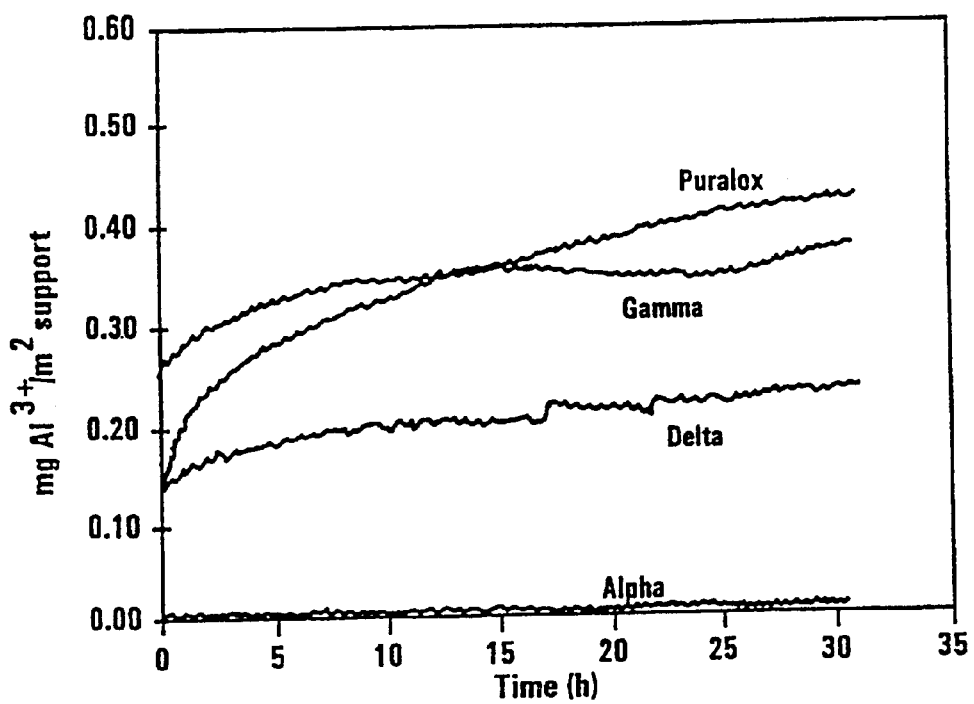
FIG. 11 shows dissolution profiles for different alumina crystal phases.

Thus, from FIG. 11, it is clear that delta alumina has a lower dissolution profile than gamma alumina, while alpha alumina has a lower dissolution profile than delta alumina. It can therefore be concluded that an alumina Fischer-Tropsch catalyst support, which mainly consists of a mixture of delta and gamma alumina, such as, for example, Condea Puralox SCCa 5/150 (trademark) alumina support would be susceptible to aqueous/acid attack and subsequent dissolution.

EXAMPLE 12

The acidity of a Fischer-Tropsch catalyst support plays an important role in the selectivity of said catalyst under Fischer-Tropsch synthesis conditions. By modifying the support with silica, as shown in Example 1, the support acidity can possibly be influenced negatively. A test reaction can determine whether the support's acidity or basicity is influenced.

The dehydration reaction rate of isopropanol over a catalyst gives a relative indication of the acidity of the catalyst:

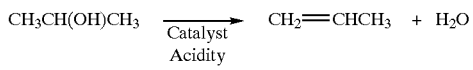

By measuring the propylene formation rate over different supports, their relative acidity can be compared.

Silica was impregnated at four different levels onto a Condea Puralox SCCa 5/150 (trademark) alumina support by using TEOS as silica source, as detailed in Example 1. After impregnation, the supports were calcined at 500° C. The silica levels were 2.5, 3.5, 8.5 and 15.6 Si atoms/nm² fresh support respectively.

Test Procedure

In each test run, 3.5 g of the modified support was loaded into a micro fixed bed reactor. The modified support was heated to 195° C. under hydrogen flow at atmospheric pressure. After the temperature had stabilized at 195° C., isopropanol was co-fed to the reactor at a fixed liquid flow rate of 30 g/h, whilst the $H_2$ flow was maintained at 12 $l_n$/h. An online GC was used to analyze the reaction products after 15 minutes online. The relative support acidity of modified support Z is defined as: (observed propylene formation rate of support Z)/(observed propylene formation rate of the fresh support), with the rates being expressed per unit surface area.

Figure 12:
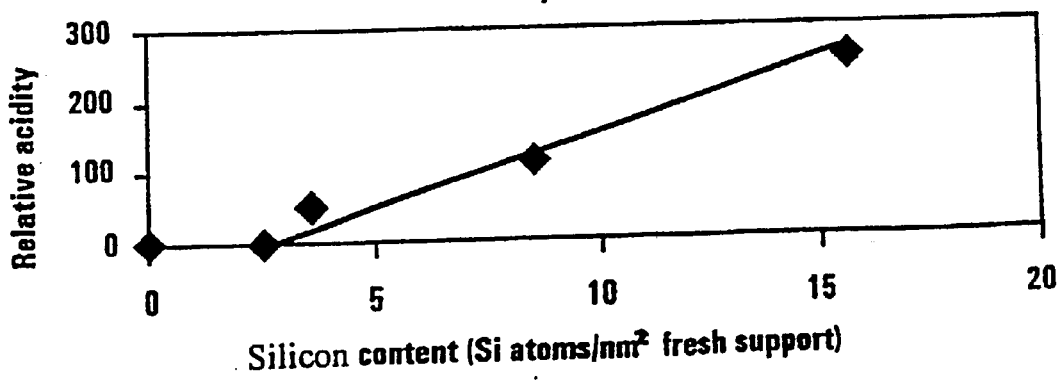
FIG. 12 shows a plot of relative support acidity against silicon content of alumina.

FIG. 12 clearly indicates that the acidity of the silicon modified supports sharply increases at a level exceeding 2.5 Si atoms/nm² of fresh alumina support. Seeing, however, that an upper silicon modification level of 2.5 Si atoms/nm² fresh alumina support is also the preferred upper Si level from a geometry influencing point of view, both of these upper Si level controlling criteria can successfully be met simultaneously.

The Inventors have thus developed a catalyst impregnated on a modified catalyst support with excellent Fischer-Tropsch synthesis behaviour, resulting in high activity and selectivity. It was surprisingly found that an increased support inertness towards an acidic aqueous attack during slurry phase impregnations, resulted in a dramatic decrease in the formation of active phase containing ultra-fines during slurry phase Fischer-Tropsch synthesis. A slurry phase Fischer-Tropsch process, using the modified supported catalyst, will thus result in a wax product containing less than 50 ppm active phase ultra fines throughout extended synthesis runs, thus reducing the cost for the catalyst used in the slurry phase Fischer-Tropsch process substantially. The problem of removing solids from the simplified due to the extreme difficulty with which separation of submicron particulates from this liquid product is achieved.

What is claimed is:

1. A method of pre-treating a catalyst support to be used in a catalyst-forming process involving impregnation of the support in neutral or acidic conditions, which method comprises introducing onto and/or into an untreated particulate catalyst support selected from the group consisting in $Al_2O_3$, titania ($TiO_2$) and magnesia (MgO), a modified component which is capable, when present in and/or on the catalyst support, of suppressing the solubility of the catalyst support in aqueous acid solutions and/or neutral aqueous solutions, said modifying component being selected from the group consisting in Si, Zr, Cu, Zn, Mn, Ba, Co, Ni and La and calcining the resultant modifying component-containing catalyst support to decompose organic groups or to form spinel structures with the support, at a temperature from 400° C. to 800° C. and for a period of from 1 minute to 4 hours, to obtain a protected modified catalyst support which is less soluble or more inert in the aqueous acid solutions and/or the neutral aqueous solutions, than the untreated catalyst support, with the modifying component being present, in the modified catalyst support particles, on the particle surfaces by being chemically bonded to the particle surfaces, provided that when the modifying component comprises Co or Zr, the calcination temperature is from 600° C. to 800° C.

2. A method according to claim 1, wherein the introduction of the modifying component onto and/or into the catalyst support includes contacting a precursor of the modifying component with the catalyst support, whereafter the calcining of the modifying component-containing modified catalyst support, to obtain the protected modified catalyst support, is effected.

3. A method according to claim 2, wherein the contacting of the precursor with the catalyst support includes dissolving the precursor in an impregnation solvent; admixing the particulate catalyst support with the resultant solution to form a treatment mixture; maintaining the treatment mixture at an elevated temperature at or near the boiling point of the impregnation solvent and at about atmospheric pressure, for from 1 minute to 20 hours; and removing excess solvent or solution under a vacuum of 0.01 to 1 bar(a) to obtain the modified catalyst support.

4. A method according to claim 3, wherein a silicon-based modifying component precursor is used so that the modifying component is Si, with the untreated catalyst support being $Al_2O_3$, and with the precursor being used in a quantity such that the silicon level in the resultant protected modified catalyst support is at least 0.06 Si atoms per square nanometer of the untreated or fresh support.

5. A method according to claim 4, wherein the untreated support is spray-dried $Al_2O_3$ and wherein the precursor is used in a quantity such that the silicon level in the resultant protected modified catalyst support is not more than 2.8 Si atoms/nm² of fresh catalyst support.

6. A method according to claim 3, wherein an inorganic cobalt compound is used as the modifying component precursor, so that the modifying component is Co.

7. A method according to claim 3, wherein an organic zirconium compound is used as the modifying component precursor, so that the modifying component is Zr.

8. A protected modified catalyst support, when obtained by the method of claim 1.

9. A method of forming a catalyst, which method comprises mixing a protected modified catalyst support obtained by the method of claim 1, with an aqueous solution of an active catalyst component or its precursor, to form a slurry, and impregnating the protected modified catalyst support with the active catalyst component or its precursor, to form the catalyst in reduced form.

10. A method according to claim 9, wherein the active catalyst component precursor is cobalt nitrate so that the active catalyst component in and on the catalyst is cobalt.

11. A method according to claim 10, wherein the mixing of the protected modified catalyst support and the active catalyst component or its precursor aqueous solution, and the impregnating, comprises subjecting a slurry of the catalyst support or carrier, water and the active catalyst component or its precursor to a sub-atmospheric pressure environment, drying the resultant impregnated carrier under a sub-atmospheric pressure environment, calcining the dried impregnated carrier, to obtain the catalyst in unreduced form, and washing the unreduced catalyst with water.

12. A method according to claim 10, wherein the support is $Al_2O_3$, and wherein the following two-stage cobalt slurry phase impregnation and calcination of the active catalyst component precursor is effected:

in a first stage or step, $(1.82xy)$ kg $Co(NO_3)_2.6H_2O$, where x is the BET pore volume of the $Al_2O_3$ in mR/g and y is the total mass of the support to be impregnated in kg, is dissolved in sufficient distilled water such that the final volume of the solution is >xy liter; this solution is heated to a temperature between 60 and 95° C.; to this solution is added the total inventory of y kg support material at atmospheric pressure whilst continuous mixing of the slurry is maintained; with the gradual application of vacuum, under continuous mixing at a temperature between 60 and 95° C., the loss on ignition (L.O.I.) content of the slurry is reduced, over 3 or more hours, from >$(136.4x)/(1+1.86x)$ mass % to a state of incipient wetness, with loss on ignition (L.O.I.) being defined as the mass % loss observed during complete calcination or complete decomposition to $Co_3O_4/Al_2O_3$; at the state of incipient wetness (L.O.I. of $(136.4x)/(1+1.86x)$), a vacuum of <20 kpa(a) is applied whilst ensuring that the temperature does not drop below 60° C. under continuous mixing; once the state of incipient wetness has been reached, vacuum drying is proceeded with in an uninterrupted fashion, at the conditions: temperature >60° C., but not higher than 95° C., and a vacuum of <20 kPa(a); vacuum drying under these specific conditions is maintained until a L.O.I. <90% of the L.O.I. value at incipient wetness has been reached; direct calcination of this dried material at 200° C. to 300° C. is then effected; and thereafter in the second stage or step, it is assumed that the BET pore volume of the first stage material is x' mR/g, and that y' kg of this material is to be impregnated for a second time, and the following procedure is adapted for proper impregnation:

a maximum of $(1.82x'y')$ kg $Co(NO_3)_2.6H_2O$, where x' is the BET pore volume of the first stage calcined material in mR/g, and y' is the total mass of the first stage calcined material to be impregnated in kg, is used during this second impregnation, and is dissolved in sufficient distilled water such that the final volume of the solution is >x'y' liter; this solution is heated to a temperature between 60 and 95° C., to this solution is added the final inventory of y' kg of the first stage calcined material is added at atmospheric pressure, whilst continuous mixing of the slurry is maintained; with the gradual application of vacuum, under continuous mixing at a temperature between 60 and 95° C., the L.O.I. content of the slurry is reduced, over 3 or more hours, to the state of incipient wetness; at the stage of incipient wetness, a vacuum of <20 kPa(a) is applied whilst simultaneously ensuring that the temperature does not drop below 60° C. under continuous mixing; once the stage of incipient wetness has been reached, vacuum drying proceeds in an uninterrupted fashion, at the conditions: temperature >60° C., but not higher than 95° C., and a vacuum of <20 kPa(a); vacuum drying under these specific conditions is maintained until a L.O.I. <90% of the L.O.I. value at incipient wetness has been reached; direct calcination of this dried material at 200° C. to 300° C. is then effected.

13. A method according to claim 12 wherein, during either, or both, of the two slurry phase cobalt impregnation steps, a water soluble precursor salt of Pt or Pd is added, as a dopant capable of enhancing the reducibility of the active component, with the mass proportion of this dopant to cobalt being between 0.01:100 and 0.3:100.

14. A catalyst, when produced by the method of claim 9.

15. A method of pre-treating a catalyst support to be used in a catalyst-forming process involving impregnation of the support in neutral or acidic conditions, which method comprises admixing an untreated particulate catalyst support selected from the group consisting in $Al_2O_3$, titania ($TiO_2$) and magnesia (MgO), with a solution of a precursor of a modifying component selected from the group consisting in Si, Zr, Cu, Zn, Mn, Ba, Co, Ni and La in an impregnation solvent, to form a treatment mixture, with the modifying component being capable, when present in and/or on the catalyst support of suppressing the solubility of the catalyst support in aqueous acid solutions and/or neutral aqueous solutions;

maintaining the treatment mixture near the boiling point of the impregnation solvent for from 1 minute to 20 hours; and removing excess solvent or solution under a vacuum of 0.01 to 1 bar(a), to obtain a modifying component-containing modified catalyst support; and calcining the modifying component-containing catalyst support to decompose organic groups or to form spinel structures with the support, at a temperature from 400° C. to 800° C. and for a period of from 1 minute to 4 hours, to obtain a protected modified catalyst support which is less soluble or more inert in the aqueous acid solutions and/or the neutral aqueous solutions than the untreated catalyst support, with the modifying component being present, in the modified catalyst support particles, on the particle surfaces by being chemically bonded to the particle surfaces, and provided that when the modifying component comprises Co or Zr, the calcination temperature is from 600° C. to 800° C.

16. A method of forming a catalyst, which method comprises in a first stage or step, dissolving $(1.82xy)$kg $Co(NO_3)_2.6H_2O$, where x is the BET pore volume of a protected modified alumina catalyst support obtained by introducing onto and/or into an untreated particulate catalyst support selected from the group consisting in $Al_2O_3$, titania ($TiO_2$) and magnesia (MgO), a modifying component which is capable, when present in and/or on the catalyst support, of suppressing the solubility of the catalyst support in aqueous acid solutions and/or neutral aqueous solutions, said modifying component being selected from the group consisting in Si, Zr, Cu, Zn, Mn, Ba, Co, Ni and La, and calcining the resultant modifying component containing catalyst support at a temperature from 400° C. to 800° C. and for a period of from 1 minute to 4 hours, thereby obtaining the protected modified catalyst support which is less soluble or more inert in the aqueous acid solutions and/or the neutral aqueous solutions than the untreated catalyst support, with the modifying component being present, in the modified catalyst support particles, on the particle surfaces by being chemically bonded to the particle surfaces, in mR/g and y is the total mass of the support to be impregnated in kg, in sufficient distilled water such that the final volume of the solution is >xy liter; heating this solution to a temperature between 60 and 95° C.; adding to this solution the total inventory of y kg support material at atmospheric pressure whilst continuous mixing of the slurry is maintained; reducing, with the gradual application of vacuum, under continuous mixing at a temperature between 60 and 95° C., the loss on ignition (L.O.I.) content of the slurry, over 3 or more hours, from >(136.4x)/(1+1.86x) mass % to a state of incipient wetness, with loss on ignition (L.O.I.) being defined as the mass % loss observed during complete calcination or complete decomposition to $Co_3O_4/Al_2O_3$; applying, at the state of incipient wetness (L.O.I. of (136.4x)/(1+1.86x)), a vacuum of <20 kpa(a) whilst ensuring that the temperature does not drop below 60° C. under continuous mixing; once the state of incipient wetness has been reached, proceeding with vacuum drying in an uninterrupted fashion, at the conditions: temperature >60° C., but not higher than 95° C., and a vacuum of <20 kPa(a); maintaining vacuum drying under these specific conditions until a L.O.I. <90% of the L.O.I. value at incipient wetness has been reached; then effecting direct calcination of this dried material at 200° C. to 300° C.; and thereafter in the second stage or step, it is assumed that the BET pore volume of the first stage material is x' mR/g, and that y' kg of this material is to be impregnated for a second time, and the following procedure is adopted for proper impregnation:

using, during this second impregnation, a maximum of (1.82x'y')kg $Co(NO_3)_2.6H_2O$, where x' is the BET pore volume of the first stage calcined material in mR/g, and y' is the total mass of the first stage calcined material to be impregnated in kg, dissolving the first stage calcined material in sufficient distilled water such that the final volume of the solution is >x'y' liter; heating this solution to a temperature between 60 and 95° C., adding to this solution the final inventory of y' kg of the first stage calcined material at atmospheric pressure, whilst continuous mixing of the slurry is maintained; reducing, with the gradual application of vacuum, under continuous mixing at a temperature between 60 and 95° C., the L.O.I. content of the slurry, over 3 or more hours, to the state of incipient wetness; at the stage of incipient wetness, applying a vacuum of <20 kPa(a) whilst simultaneously ensuring that the temperature does not drop below 60° C. under continuous mixing; once the stage of incipient wetness has been reached, proceeding with vacuum drying in an uninterrupted fashion, at the conditions: temperature >60° C., but not higher than 95° C., and a vacuum of <20 kPa(a); maintaining vacuum drying under these specific conditions until a L.O.I. <90% of the L.O.I. value at incipient wetness has been reached; then effecting direct calcination of this dried material at 200° C. to 300° C.

17. A method according to claim 16, wherein, during either, or both, of the two slurry phase cobalt impregnation steps, a water soluble precursor salt of Pt or Pd is added, as a dopant capable of enhancing the reducibility of the active component, with the mass proportion of this dopant to cobalt being between 0.01:100 and 0.3:100.

18. A catalyst, produced by the method of claim 16.

* * * * *